US008758839B2

(12) United States Patent
Faller et al.

(10) Patent No.: US 8,758,839 B2
(45) Date of Patent: Jun. 24, 2014

(54) MAGNOLIA EXTRACT CONTAINING COMPOSITIONS

(75) Inventors: Jim Faller, Williamsville, NY (US);
David Gan, Southlake, TX (US);
Michelle Hines, Lewisville, TX (US);
Lisa Mangos, Carrolton, TX (US)

(73) Assignee: Mary Kay Inc., Dallas, TX (US)

( * ) Notice: Subject to any disclaimer, the term of this patent is extended or adjusted under 35 U.S.C. 154(b) by 0 days.

(21) Appl. No.: 13/297,755

(22) Filed: Nov. 16, 2011

(65) Prior Publication Data
US 2012/0058209 A1 Mar. 8, 2012

Related U.S. Application Data

(63) Continuation of application No. 12/706,557, filed on Feb. 16, 2010, now Pat. No. 8,084,066, which is a continuation of application No. 12/048,953, filed on Mar. 14, 2008, now Pat. No. 7,744,932.

(60) Provisional application No. 60/912,793, filed on Apr. 19, 2007.

(51) Int. Cl.
*A61K 36/00* (2006.01)
*A61K 36/575* (2006.01)
*A61K 36/87* (2006.01)

(52) U.S. Cl.
USPC ............ 424/766; 424/775; 424/776; 424/725

(58) Field of Classification Search
None
See application file for complete search history.

(56) References Cited

U.S. PATENT DOCUMENTS

| | | | |
|---|---|---|---|
| 3,755,560 A | 8/1973 | Dickert et al. | 424/78 |
| 4,308,179 A | 12/1981 | Celli | 252/522 |
| 4,421,769 A | 12/1983 | Dixon et al. | 424/358 |
| 4,459,285 A | 7/1984 | Grollier et al. | 424/74 |
| 4,581,230 A | 4/1986 | Grollier et al. | 424/74 |
| 4,650,813 A | 3/1987 | Kooda et al. | 514/701 |
| 4,880,621 A | 11/1989 | Grollier et al. | 424/74 |
| 5,011,681 A | 4/1991 | Ciotti et al. | 424/81 |
| 5,073,545 A | 12/1991 | Arima et al. | 514/27 |
| 5,614,489 A | 3/1997 | Mohammadi et al. | 514/2 |
| 5,676,956 A | 10/1997 | Duffy et al. | 424/401 |
| 5,869,540 A | 2/1999 | Smith | 514/783 |
| 5,989,596 A | 11/1999 | Bresson-Rival et al. | 424/711 |
| 6,117,915 A | 9/2000 | Pereira et al. | 516/57 |
| 6,153,208 A | 11/2000 | McAtee et al. | 424/402 |
| 6,159,487 A | 12/2000 | Znaiden et al. | 424/402 |
| 6,190,678 B1 | 2/2001 | Hasenoehrl et al. | 424/401 |
| 6,203,782 B1 | 3/2001 | Eliaz et al. | 424/70.1 |
| 6,280,751 B1 | 8/2001 | Fletcher et al. | 424/401 |
| 6,284,234 B1 | 9/2001 | Neimiec et al. | 424/78.07 |
| 6,290,938 B1 | 9/2001 | Tanner et al. | 424/59 |
| 6,338,855 B1 | 1/2002 | Albacarys et al. | 424/409 |
| 6,419,913 B1 | 7/2002 | Niemiec et al. | 424/78.07 |
| 6,495,498 B2 | 12/2002 | Niemiec et al. | 510/122 |
| 6,524,627 B1 | 2/2003 | Kim et al. | 424/741 |
| 6,582,735 B2 | 6/2003 | Stogniew et al. | 424/725 |
| 6,589,537 B2 | 7/2003 | Harbeck | 424/400 |
| 6,632,422 B2 | 10/2003 | Burry et al. | 424/65 |
| 6,645,506 B1 | 11/2003 | Farmer | 424/260.1 |
| 6,657,100 B1 | 12/2003 | Underhill et al. | 604/361 |
| 6,673,844 B2 | 1/2004 | Kumamoto et al. | 514/699 |
| 6,703,004 B2 | 3/2004 | Narasimhan et al. | 424/62 |
| 6,749,860 B2 | 6/2004 | Tyrrell et al. | 424/404 |
| 6,762,158 B2 | 7/2004 | Lukenbach | 510/122 |
| 6,774,260 B2 | 8/2004 | Bledsoe et al. | 560/193 |
| 6,814,987 B2 | 11/2004 | Stogniew et al. | 424/769 |
| 6,825,161 B2 | 11/2004 | Shefer | 510/438 |
| 6,858,202 B2 | 2/2005 | Niemiec et al. | 424/70.12 |
| 6,905,692 B2 | 6/2005 | Farmer | 424/260.1 |
| 6,908,889 B2 | 6/2005 | Niemiec et al. | 510/130 |
| 6,919,477 B2 | 7/2005 | Bledsoe et al. | 560/193 |
| 6,932,975 B2 | 8/2005 | Ishikawa et al. | 424/401 |
| 7,074,747 B1 | 7/2006 | Lukenbach et al. | 510/135 |
| 7,125,835 B2 | 10/2006 | Bennett et al. | 512/4 |
| 7,160,560 B2 | 1/2007 | Pinnell | 424/725 |
| 7,160,852 B2 | 1/2007 | Levorse, Jr. et al. | 512/14 |
| 7,169,379 B2 | 1/2007 | Kouzuki et al. | 424/59 |
| 7,208,460 B2 | 4/2007 | Shefer et al. | 510/441 |
| 7,347,985 B2 | 3/2008 | Maxwell et al. | 424/58 |
| 2001/0001665 A1 | 5/2001 | Harbeck | 424/401 |
| 2001/0001666 A1 | 5/2001 | Harbeck | 424/401 |
| 2002/0034489 A1 | 3/2002 | Wiegland et al. | 424/70.24 |
| 2002/0076456 A1 | 6/2002 | Stogniew et al. | 424/769 |
| 2002/0120242 A1 | 8/2002 | Tyrrell et al. | 604/364 |
| 2003/0069148 A1 | 4/2003 | Booker et al. | 510/130 |
| 2003/0105445 A1 | 6/2003 | Lange et al. | 604/358 |

(Continued)

FOREIGN PATENT DOCUMENTS

| | | |
|---|---|---|
| EP | 0 965 328 | 12/1999 |
| EP | 0 989 181 | 3/2000 |

(Continued)

OTHER PUBLICATIONS

Patocka et al, Expectations of biologically active compounds of the genus *Magnolia* in biomedicine. Journal of Applied Biomedicine (2006), 4(4), 171-178.*
Office Communication issued in Eurasian Divisional Patent Application No. 201171401, dated Jul. 18, 2012.
Office Communication, issued in Canadian Patent Application No. 2,684,601, mailed on May 9, 2012.
(Abstract of) Wang et al., "Anti-inflammatory mechanism of the volatile oil of *Magnolia biondii* pamp," *Chinese Journal of Veterinary*, 2005.
"L'Oreal keeps new beauty products coming; new products; brief article," *Chain Drug Review*, 23(11):143, 2001.
"L'Oreal meets needs of older consumers; new skin care product; brief article," *Chain Drug Review*, 23(6):31, 2001.
"Natural new ingredients," Household & Personal Products Industry, Rodman Publications, Inc., 43(6):78(7), Jun. 2006.
"Naturals new ingredients," *Household & Personal Products Industry*, 38(6):94, 2001.

(Continued)

*Primary Examiner* — Qiuwen Mi
(74) *Attorney, Agent, or Firm* — Fulbright & Jaworski LLP

(57) ABSTRACT

Disclosed is a composition and method for its use that includes *Magnolia* bark extract, *vitis vinifera* extract, tocopherol or tocopherol acetate, and hydrogenated lecithin, lecithin, or dextrin.

4 Claims, No Drawings

(56) References Cited

U.S. PATENT DOCUMENTS

| | | | |
|---|---|---|---|
| 2003/0130636 A1 | 7/2003 | Brock et al. | 604/358 |
| 2003/0190302 A1 | 10/2003 | Frantz et al. | 424/70.1 |
| 2003/0198610 A1 | 10/2003 | Nakayama et al. | 424/401 |
| 2003/0206953 A1 | 11/2003 | Dvoracek | 424/766 |
| 2003/0232091 A1 | 12/2003 | Shefer et al. | 424/490 |
| 2004/0053860 A1 | 3/2004 | Buchholz et al. | 514/456 |
| 2004/0071747 A1 | 4/2004 | Kume et al. | 424/401 |
| 2004/0081675 A1 | 4/2004 | Wirth et al. | 514/183 |
| 2004/0081681 A1 | 4/2004 | Vromen | 424/449 |
| 2004/0116539 A1 | 6/2004 | Biercevicz et al. | 516/21 |
| 2004/0167046 A1 | 8/2004 | Lukenbach et al. | 510/135 |
| 2004/0167479 A1 | 8/2004 | Warren et al. | 604/289 |
| 2004/0223942 A1 | 11/2004 | Fujimura et al. | 424/70.1 |
| 2004/0228934 A1 | 11/2004 | Stogniew et al. | 424/769 |
| 2004/0265395 A1 | 12/2004 | Sun et al. | 424/617 |
| 2004/0267169 A1 | 12/2004 | Sun et al. | 601/15 |
| 2004/0267231 A1 | 12/2004 | Sun et al. | 604/500 |
| 2004/0267232 A1 | 12/2004 | Sun et al. | 604/500 |
| 2004/0267236 A1 | 12/2004 | Sun et al. | 604/501 |
| 2004/0267237 A1 | 12/2004 | Sun et al. | 604/501 |
| 2005/0004508 A1 | 1/2005 | Sun et al. | 604/20 |
| 2005/0004509 A1 | 1/2005 | Sun et al. | 604/20 |
| 2005/0004550 A1 | 1/2005 | Sun et al. | 604/501 |
| 2005/0009717 A1 | 1/2005 | Lukenbach | 510/136 |
| 2005/0010161 A1 | 1/2005 | Sun et al. | 604/20 |
| 2005/0010192 A1 | 1/2005 | Sun et al. | 604/501 |
| 2005/0015042 A1 | 1/2005 | Sun et al. | 604/20 |
| 2005/0020468 A1 | 1/2005 | Frantz et al. | 510/424 |
| 2005/0025737 A1 | 2/2005 | Sebagh | 424/74 |
| 2005/0031718 A1 | 2/2005 | Zhu et al. | 424/765 |
| 2005/0100524 A1 | 5/2005 | Springstead | 424/74 |
| 2005/0106112 A1 | 5/2005 | Boyd et al. | 424/49 |
| 2005/0123578 A1 | 6/2005 | Ishikawa et al. | 424/401 |
| 2005/0129783 A1 | 6/2005 | McCleary et al. | 514/283 |
| 2005/0147631 A1 | 7/2005 | Goldstein et al. | 424/401 |
| 2005/0148910 A1 | 7/2005 | Skover et al. | 601/46 |
| 2005/0148996 A1 | 7/2005 | Sun et al. | 604/501 |
| 2005/0154066 A1 | 7/2005 | Fujii et al. | 514/183 |
| 2005/0175653 A1 | 8/2005 | Grollier et al. | 424/59 |
| 2005/0175717 A1 | 8/2005 | De La Mettrie et al. | 424/725 |
| 2005/0214328 A1 | 9/2005 | Zeldis et al. | 514/323 |
| 2005/0255076 A1 | 11/2005 | Santo et al. | 424/756 |
| 2005/0260289 A1 | 11/2005 | Santo et al. | 424/757 |
| 2005/0271608 A1 | 12/2005 | Gupta | 424/62 |
| 2005/0271692 A1 | 12/2005 | Gervasio-Nugent et al. | 424/401 |
| 2005/0281757 A1 | 12/2005 | Ibrahim et al. | 424/49 |
| 2005/0281772 A1* | 12/2005 | Bromley et al. | 424/70.14 |
| 2006/0003030 A1 | 1/2006 | Chun-Ying et al. | 424/725 |
| 2006/0013779 A1 | 1/2006 | Dodds et al. | 424/48 |
| 2006/0018867 A1 | 1/2006 | Kawasaki et al. | 424/70.122 |
| 2006/0018975 A1 | 1/2006 | Talbott | 424/729 |
| 2006/0024339 A1 | 2/2006 | Murad | 424/401 |
| 2006/0045896 A1 | 3/2006 | Morariu | 424/401 |
| 2006/0052438 A1 | 3/2006 | Ho et al. | 514/453 |
| 2006/0062816 A1 | 3/2006 | Gatto et al. | 424/404 |
| 2006/0062859 A1 | 3/2006 | Blum et al. | 424/725 |
| 2006/0074108 A1 | 4/2006 | Gupta | 514/332 |
| 2006/0089413 A1 | 4/2006 | Schmaus et al. | 514/563 |
| 2006/0127412 A1 | 6/2006 | Kakuo et al. | 424/725 |
| 2006/0134024 A1 | 6/2006 | Trivedi et al. | 424/750 |
| 2006/0134095 A1 | 6/2006 | Ito et al. | 424/125 |
| 2006/0135627 A1 | 6/2006 | Frantz et al. | 516/58 |
| 2006/0140885 A1 | 6/2006 | Gaffar et al. | 424/58 |
| 2006/0141058 A1 | 6/2006 | Talbott | 424/725 |
| 2006/0141075 A1 | 6/2006 | Talbott | 424/725 |
| 2006/0239928 A1 | 10/2006 | Heit et al. | 424/45 |
| 2006/0251608 A1 | 11/2006 | Wachsberg et al. | 424/725 |
| 2006/0263459 A1 | 11/2006 | Zhu et al. | 424/725 |
| 2006/0275222 A1 | 12/2006 | Dodds et al. | 424/48 |
| 2007/0003536 A1* | 1/2007 | Zimmerman et al. | 424/94.4 |
| 2007/0041922 A1* | 2/2007 | Reinhart et al. | 424/70.7 |
| 2007/0134171 A1 | 6/2007 | Dodds et al. | 424/775 |
| 2007/0154863 A1 | 7/2007 | Cai et al. | 433/89 |
| 2007/0160687 A1 | 7/2007 | Kim et al. | 424/757 |
| 2007/0166407 A1 | 7/2007 | Tanaka et al. | 424/725 |
| 2007/0183990 A1 | 8/2007 | Dodds et al. | 424/775 |
| 2007/0196296 A1 | 8/2007 | Osborne et al. | 424/725 |
| 2007/0231403 A1 | 10/2007 | Park et al. | 424/539 |
| 2008/0107610 A1 | 5/2008 | Maxwell et al. | 424/48 |
| 2008/0260869 A1 | 10/2008 | Faller et al. | 424/736 |
| 2009/0156666 A1 | 6/2009 | Raederstorff et al. | 514/459 |

FOREIGN PATENT DOCUMENTS

| | | |
|---|---|---|
| EP | 1 066 009 | 8/2003 |
| EP | 1 550 451 | 7/2005 |
| EP | 1 595 936 | 11/2005 |
| EP | 1 604 647 | 12/2005 |
| JP | 04 082814 | 3/1992 |
| JP | 04 082816 | 3/1992 |
| JP | 2001 122730 | 5/2001 |
| JP | 2002 104924 | 4/2002 |
| JP | 2002104924 A * | 4/2002 |
| JP | 2002-154922 | 5/2002 |
| JP | 2003 146876 | 5/2003 |
| JP | 2004 231550 | 8/2004 |
| JP | 2005 194245 | 7/2005 |
| JP | 2005 206466 | 8/2005 |
| JP | 2006 160630 | 6/2006 |
| JP | 2006273811 | 10/2006 |
| KR | 2005026297 A * | 3/2005 |
| RU | 2207108 | 6/2003 |
| WO | WO 97/35599 | 10/1997 |
| WO | WO 98/50005 | 11/1998 |
| WO | WO 99/20289 | 4/1999 |
| WO | WO 99/49878 | 10/1999 |
| WO | WO 00/64278 | 11/2000 |
| WO | WO 00/64279 | 11/2000 |
| WO | WO 01/01816 | 1/2001 |
| WO | WO 01/01950 | 1/2001 |
| WO | WO 01/01952 | 1/2001 |
| WO | WO 02/11690 | 2/2002 |
| WO | WO 02/34183 | 5/2002 |
| WO | WO 02/069992 | 9/2002 |
| WO | WO 02/091848 | 11/2002 |
| WO | WO 02/092027 | 11/2002 |
| WO | WO 02/092038 | 11/2002 |
| WO | WO 04/000235 | 12/2003 |
| WO | WO 2004/064769 | 8/2004 |
| WO | WO 2004/091368 | 10/2004 |
| WO | WO 2005/020950 | 3/2005 |
| WO | WO 2005/034903 | 4/2005 |
| WO | WO 2005/058476 | 6/2005 |
| WO | WO 2005/067627 | 7/2005 |
| WO | WO 2005/074963 | 8/2005 |
| WO | WO 2005/091991 | 10/2005 |
| WO | WO 2005/095462 | 10/2005 |
| WO | WO 2005/115326 | 12/2005 |
| WO | WO 2005/123101 | 12/2005 |
| WO | WO 2006/009737 | 1/2006 |
| WO | WO 2006/010606 | 2/2006 |
| WO | WO 2006/020131 | 2/2006 |
| WO | WO 2006/040349 | 4/2006 |
| WO | WO 2006/045760 | 5/2006 |
| WO | WO 2006/053415 | 5/2006 |
| WO | WO 2006/053688 | 5/2006 |
| WO | WO 2006/053912 | 5/2006 |
| WO | WO 2006/069209 | 6/2006 |
| WO | WO 2006/071653 | 7/2006 |
| WO | WO 2007/011504 | 1/2007 |
| WO | WO 2007/011674 | 1/2007 |
| WO | WO 2007/061691 | 5/2007 |
| WO | WO 2007/064505 | 6/2007 |
| WO | WO 2007/064519 | 6/2007 |
| WO | WO 2007/126651 | 11/2007 |
| WO | WO 2007/144325 | 12/2007 |
| WO | WO 2008/006581 | 1/2008 |
| WO | WO 2008/006582 | 1/2008 |
| WO | WO 2008/006589 | 1/2008 |
| WO | WO 2008/016855 | 2/2008 |

OTHER PUBLICATIONS

"Prescriptives super line preventor + intensive eye treatment," Product Alert, Marketing Intelligence Service Ltd., 33(12):0, Jun. 2003.

(56) References Cited

OTHER PUBLICATIONS

"Skin disorders," from Merek Manual, retrieved from http://ww.merek.com/mmhe/sec18.html, retrieved on Feb. 3, 2009.
"Vitiligo," from Merek Manual, retrieved from http://ww.merek.com/mmhe/sec18.html, retrieved on Feb. 3, 2009.
Bai et al., "Honokiol, a small molecular weight natural product, inhibits angiogenesis in vitro and tumor growth in vivo," *J. Biol. Chem.*, 278(37):35501-35507, 2003.
Cleaver, "Defective repair replication of DNA in xeroderma pigmentosum," *Nature*, 218:652-6, 1968, Abstract.
Figlar and Nooteboom, "Notes on Magnoliaceae IV," *Blumea*, 49:87-100, 2004.
Granger et al., "Association between dietary fat and skin cancer in an Australian population using case-control and cohort study designs," *BMC Cancer*, 6:1-7, 2006.
Hobbs, "Adaptogens: all-purpose herbs; class of herbs that strengthen the body's immune function and restore balance to all bodily systems; includes related information on eleuthero ginseng, on wie chi soup, and on various other adaptogen herbs," *East West*, 21(7):54, 1991.
International Cosmetic Ingredient Dictionary, 10$^{th}$ Ed., 2004.
Jullien, "A new treatment for psoriasis," *Nouvelles Dermatelogiques*, 25:264-72, 2006, Abstract.
Kim et al., "Anti-itching and anti-inflammatory composition for treating atopic dermatitis comprising extracts of natural herbs having no harmful effects to human," Database WPI Week 200676, Thomas Scientific, London, GB, 2006-741733, Abstract.
Maemura et al., "Skin external prepn. for acne treatment—contg. magnolol and/or honokiol or magnolia obovata soln. extract with organic solvent, for low toxicity," WPI/Thomson, Jan. 1, 1900, Abstract.
McCutcheon's Emulsifiers & Detergents North American Edition, 2001.
Office Communication, issued in International Application No. PCT/US2008/057091, dated Nov. 26, 2008.
Office Communication, issued in International Application No. PCT/US2008/057091, dated Jan. 28, 2009.
Office Communication, issued in Eurasian Patent Application No. 200901364, dated May 24, 2011. (English translation).
Office Communication, issued in European Application No. 08 743 926.1-2108, mailed Feb. 5, 2010.
Office Communication, issued in European Application No. 08 743 926.1-2108, mailed May 26, 2011.
Office Action, issued in U.S. Appl. No. 12/048,953, mailed Nov. 7, 2008.
Office Action, issued in U.S. Appl. No. 12/048,953, mailed Mar. 9, 2009.
Office Action, issued in U.S. Appl. No. 12/048,953, mailed Jun. 26, 2009.
Office Action, issued in U.S. Appl. No. 12/706,557, mailed on Jun. 20, 2011.
Office Action, issued in U.S. Appl. No. 12/706,557, mailed on Jul. 25, 2011.
Office Action, issued in U.S. Appl. No. 12/907,362, mailed on May 4, 2011.
Office Action, issued in U.S. Appl. No. 12/907,362, mailed on Apr. 7, 2011.
Papadopoulos and Walker, "Personality, coping and sex as psychosocial aspects of psoriatic arthropathy," *Dermatology and Psychosomatics*, 4:27-32, 2003.
Schiltz et al., "Retinoic Acid Induces Cyclic Changes in Epidermal Thickness and Dermal Collagen and Glycosaminoglycan Biosynthesis Rates," *J. Investigative Dermatology*, 87:663-667, 1986.
Yu and Chang, "Effects of long-term oral administration of polymeric microcapsules containing tyrosinase on maintaining decreases systemic tyrosine levels in rats," *J. Pharma. Sci.*, 93:831-7, 2004.
"Ghumra-e-Karm-e-Barri", Ziya Al-Din Abdullah Ibn Al-Baitar; Al-Jaam'e-li-Mufradaat-al-Advia-wal-Aghzia, vol. IV (13$^{th}$ Century AD) Matba Amra, Cairo Egypt, p. 57, 1874. (Translation).
"Madhukarkati Mula Guna" Madanapala; Madanapalanighantauh—Translated by Rama Prasad; Khemaraj Shri Krishnadas, Prakashan, Bombay, p. 134, 1998.
"Malkh E Daryai Bara E Zimaad", Mohammad Najmul Ghani Khan; Khazaain-al-Avid, vol. III (20$^{th}$ century AD), Nadeem Yuns Printer/Sheikh Mohd Basheeer & Sons, Lahore, p. 830, 1926. (Translation).
"Marookh Khosha-e-Angoor", Ziya Al-Din Abdullah Ibn Al-Baitar; Al-Jaam'e-li-Mufradaat-al-Advia-wal-Aghzia, vol. IV (13$^{th}$ Century AD), Matba Amra, Cairo, Egypt, p. 57, 1874. (Translation).
"Taraavish-e-Shaakh-e-Angoor", Mohammad Najmual Ghani Khan; Khazaain-al-Adivia, vol. I (20$^{th}$ century AD), Nadeem Yunus Printer/Sheikh Mohd Basheer & Sons, Lahore, p. 625, 1911. (Translation).
"Tila Bara-e-Baras Wa Daa-al-saghlab", Mohammad Azam Khan; Muheet Azam vol. II (Part II) (19$^{th}$ century AD, Matba Nizami, Kanpur, p. 37, 1898. (Translation).
"Zimaad-e-Kishneez", Ziya Al-Din Abdullah Ibn Al-Baitar; Al-Jaam'e-li-Mufradaat-al-Advia-wal-Aghzia, vol. IV (13$^{th}$ Century AD) Matba Amra, Cairo Egypt, p. 68, 1874. (Translation).
Avon, "2-Part Eye Lift Gel and Cream", MINTEL Database GPND; Accession No. 665510, dated Mar. 2007.
Billy Jealousy, "Wipeout Eye Cream", MINTEL Database GPND; Accession No. 563942, dated Jul. 2006.
Communication of Third Party Observations issued in European Application No. 11190655.8, dated Feb. 22, 2013.
Extended European Search Report issued in European Application No. 11190655.8, dated Oct. 23, 2012.
Grassroots Life, "Balm and Cream for Eyes", MINTEL Database GNPD; Accession No. 10237663, Oct. 2005.
Organdy Laboratories, "Aging Eye Film", MINTEL Database GPND; Accession No. 370671, dated Jun. 2005.
Origins Natural Resources, "Mega-Mushroom Eye Serum", MINTEL Database GPND; Accession No. 653604, dated Jan. 2007.
Ultima II, "Bio Feeling Facial Care", MINTEL Database GPND; Accession No. 146702, dated Apr. 2002.
*Magnolia biondii* in He'nan, Wang Ying, He'nan Science and Technology, p. 33, Jul. 30, 1989.
Office Communication issued in China, Patent Application No. 200880020961.1, dated May 19, 2013.

\* cited by examiner

MAGNOLIA EXTRACT CONTAINING COMPOSITIONS

CROSS-REFERENCE TO RELATED APPLICATIONS

This application is a continuation of U.S. application Ser. No. 12/706,557, filed Feb. 16, 2010, which is a continuation of U.S. application Ser. No. 12/048,953, filed Mar. 14, 2008 (now U.S. Pat. No. 7,744,932), which claims the benefit of U.S. Provisional Application Ser. No. 60/912,793, filed Apr. 19, 2007. The contents of these applications are incorporated by reference.

BACKGROUND OF THE INVENTION

A. Field of the Invention

The present invention relates generally to skin care compositions. In non-limiting aspects, the compositions can be used to treat skin conditions such as telangiectasia, eye circles, and puffy eyes. In certain embodiments, the compositions can include a *Magnolia* extract and can be incorporated into cosmetic products.

B. Background of the Invention

Ageing, chronic exposure to adverse environmental factors, malnutrition, fatigue, etc., can change the visual appearance, physical properties, or physiological functions of skin in ways that are considered visually undesirable. Some notable changes include the appearance spider veins, eye circles (e.g., dark circles under the eye), and puffy eyes. Other changes include the development of aged or environmentally damaged skin which can include the appearance fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

1. Spider Veins

Spider veins (i.e., telangiectasias or sunburst varicosities) are formed by the dilation of a small group of blood vessels located close to the surface of the skin. Although they can appear anywhere on the body, spider veins are most commonly found on the face and legs. They can be visible to the naked eye and typically appear as unsightly clusters of red, blue or purple veins on the thighs, calves, and ankles of people. It is estimated that over half of the adult female population suffers from this cosmetic problem. Factors that can contribute to the development of spider veins include heredity, pregnancy, and other events that cause hormonal shifts, weight gain, occupations or activities that require prolonged sitting or standing, and the use of certain medications.

Typical methods for treating spider veins is through cosmetic surgery (e.g., sclerotherapy, laser surgery, electrodesiccation, surgical ligation, and ambulatory phlebectomy). For instance, sclerotherapy is a surgical procedure where veins are injected with a sclerosing solution, which causes them to collapse and fade from view. Risks associated with sclerotherapy include the formation of blood clots in the veins, severe inflammation, adverse allergic reactions to the sclerosing solution, and skin injury that can lead to permanent scarring. Further, it is common to develop irregular skin pigmentation in the treated areas (e.g., brownish splotches) that can take several months to fade. Another problem associated with sclerotherapy is "telangiectatic matting," where fine reddish blood vessels appear around the treated area, requiring further injections. Other surgical methods can have similar side effects.

2. Eye Circles and Puffy Eyes

The skin around the periorbital area (i.e., around the eyes) is thin and delicate. Like all skin, the periorbital area is webbed with tiny capillaries. Blood sometimes leaks from these capillaries which can cause the appearance of dark circles under the eye. Other known causes dark under eye circles include UV exposure (e.g., exposure to the sun can increase natural melanin levels and draws the melanin to the surface of the skin, making it darker), ageing (e.g., with age, the skin around the eyes can become even thinner which makes dark under eye circles become more pronounced), fatigue (being tired can make skin paler which makes dark circles look darker), allergies (e.g., allergic reactions can cause smudges in the under eye area and conditions that causes a person to rub their eyes can make dark circles worse because scratching or rubbing can darken the skin), pregnancy or menstruation (e.g., skin becomes pale during pregnancy and menstruation which makes dark circles look darker), and inadequate nutrition (e.g., lack of key nutrients such as iron can cause dark under eye circles).

One method for treating under eye circles includes topical application of a composition having hydroquinone. Hydroquinone, however, can be toxic, and it may actually cause hyper-pigmentation and make the dark circles darker. Cosmetic concealers can be used to hide the dark circles. Unfortunately, the dark circles become visible again once the concealer is removed. Chamomile has also been used, but can cause allergic reactions.

As for puffy eyes, this is a condition where the skin under the eyes swells which can be visually undesirable. Puffy eyes can be caused by several factors including increased vascularization, leaky capillaries, thinning/slackening skin which can fill up with more fluid, loss of the fat pad under the eye which can contribute to under eye bags, and allergies, dusts, and pollutants which can trigger a release of chemicals thereby swelling the tissue around the eyes.

One method of treating puffy eyes includes washing the face with cold water to reduce swelling. Other treatments include dietary restrictions (e.g., limiting the intake of salt), placing slices of cucumbers on the eyes, or placing tea bags in cold water and subsequently placing the bags on the eyes. These treatment options can be limiting in that the effects can oftentimes be negligible or short-lived.

3. Aged or Environmentally Damaged Skin

Several different approaches have been used to treat damaged skin caused by aging, environmental factors, chemicals, or malnutrition. One approach involves the use of specific agents to directly stimulate or inhibit selected biochemical targets. Examples include the use of retinoids to stimulate collagen and glycosaminoglycan synthesis by fibroblasts (Schiltz, et al., 1986). Another approach is to use agents or processes that stimulate the rate at which the epidermis replaces itself, a process known as epidermal cell renewal. Increases in epidermal cell renewal rates usually result from a more rapid rate of replication of epidermal basal cells, and can be caused by diverse stimuli such as chemical or physical injury, adverse environmental conditions, or direct stimulators of basal cell division.

Several of the above methods have been shown to have various drawbacks, such as significant irritation to the skin or skin toxicity. In addition, most of these methods involve the invocation of chronic damage to the skin, which sets up repair mechanisms. For most of the existing treatments, there will be a period of time, up to several weeks or months, during which the skin becomes irritated and after which tolerance sets in and the symptoms of irritation may decrease and/or cease.

SUMMARY OF THE INVENTION

The present invention provides compositions and methods that can be used to treat the appearance of a person's skin.

In one embodiment, there is disclosed a topical skin care composition that includes, consists essentially of, or consists of at least one of the following ingredients: *Magnolia* extract; honokiol, magnolol, *humulus lupulus* extract, hesperidin methyl chalcone, gotu kola (*centella asiatica* extract), dipeptide valyl-tryptophane, palmitoyl tetrapeptide-3, *corylus avellana* bud extract, *cucumis sativa* extract, *morus alba* extract, *hibiscus sabdariffa* flower extract, *vitis vinifera* extract, ascorbyl glucoside, *citrus medica limonum* extract, *avena sativa* kernel extract, hydrolyzed soy protein, aniseed myrtle extract, *tasmania lanceolata* leaf extract, *artemisia abrotanum* extract, *citrus grandis* fruit extract, or apigenin. These ingredients can be isolated or purified prior to their inclusion in a corresponding composition. It is contemplated that compositions of the present invention can include at least 2, 3, 4, 5, 6, 7, 8, 9, or more of these ingredients in any different combination. The combination of ingredients can be formulated into blends and subsequently added to the composition. Non-limiting examples of *Magnolia* species from which the *Magnolia* extract can be obtained include *Magnolia acuminata, Magnolia ashei, Magnolia biondii, Magnolia cylindrica, Magnolia cambellii, Magnolia denudata, Magnolia fraseri, Magnolia grandiflora, Magnolia hypoleuca, Magnolia kobus, Magnolia hliiflora, Magnolia loegneri, Magnolia macrophylla, Magnolia officinalis, Magnolia pyramidata, Magnolia sargentiana, Magnolia seiboldii, Magnolia soulangiana, Magnolia sprengeri, Magnolia stellata, Magnolia tripetala, Magnolia virginiana, Magnolia zenii,* and *Michelia figo*. In certain embodiments, the composition can include a *Magnolia* extract and isolated or purified honokiol or magnolol or a combination of all three. The *Magnolia* extract in particular embodiments is *Magnolia biondii* extract. In other aspects, the composition can include *Magnolia* extract and *humulus lupulus* extract, *Magnolia* extract and hesperidin methyl chalcone and gotu kola, *Magnolia* extract and dipeptide valyl-tryptophane, *Magnolia* extract and palmitoyl tetrapeptide-3, *Magnolia* extract and *corylus avellana* bud extract, *Magnolia* extract and a botanical blend comprising *cucumis sativa* extract, *morus alba* extract, *hibiscus sabdariffa* flower extract, and *vitis vinifera* extract, *Magnolia* extract and ascorbyl glucoside, *citrus medica limonum* extract, and *cucumis sativa* extract, *Magnolia* extract and a blend of *avena sativa* kernel extract, hydrolyzed soy protein, aniseed myrtle extract, *tasmania lanceolata* leaf extract, and *hibiscus sabdariffa* flower extract, *Magnolia* extract and *artemisia abrotanum* extract, *Magnolia* extract and *citrus grandis* fruit extract, or *Magnolia* extract and isolated or purified apigenin. In certain aspects, the *citrus grandis* fruit extract includes at least 90% by weight of apigenin. The compositions can also include a cooling agent (e.g., an agent that provides a cooling sensation when applied to the skin. The cooling agent can be those known in the art such as, for example, menthol or menthol derivatives (e.g., menthyl lactate and menthone glycerin acetal).

In certain aspects, the compositions can be formulated to have a pH of about less than 4.0, or 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, to about 12.0, or more, or any range or integer derivable therein. In other aspects, the compositions can be formulated into a cosmetic product (e.g., skin cleanser, moisturizer, concealer, etc.). The composition can be comprised in a cosmetic vehicle (e.g., an emulsion, cream, lotion, solution, anhydrous base, gel, ointment, etc.). The composition can be in a dry, powdered, liquid, solid, semi-solid, spray, or aerosol form. It is contemplated that the compositions of the present invention can be used in combination with other cosmetic products (e.g., a composition of the present invention can be formulated into a concealer product which can be used in conjunction with a foundation product). The compositions can be formulated for application to skin at least 1, 2, 3, 4, 5, 6, 7, or more times per day.

As described throughout this specification, the ingredients in compositions of the present invention can be present within the compositions in a variety of amounts. The amounts can be measured by total weight or volume of the composition. By way of example only, an ingredient can be included into the composition at 0.0001, 0.001, 0.01, 0.1, 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99%, or more, or any range or integer derivable therein, by weight or volume of the total composition. In certain aspects, *Magnolia* extract can be in a composition from about 0.1% to about 10.0% by weight. The ratio of any ingredient within the composition when compared to another ingredient can be from about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 50:1, 60:1, 70:1, 80:1, 90:1, 100:1, or more or any number derivable therein, by weight or volume of the total composition. In other aspects, the ratio of any ingredient within the composition when compared to another ingredient can be from about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:50, 1:60, 1:70, 1:80, 1:90, 1:100, or more or any number derivable therein, by weight or volume of the total composition.

It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc.).

The compositions of the present invention can include additional ingredients that can be included into cosmetic or pharmaceutical compositions. As explained throughout this specification, non-limiting examples of additional ingredients can include essential oils, volatile, and non-volatile oils, thickening agents, surfactants, preservatives, silicone containing compounds, absorbents, adsorbents, chelating agents, lubricants, solvents, moisturizers (including, e.g., emollients, humectants, film formers, occlusive agents, and agents that affect the natural moisturization mechanisms of the skin), water repellents, anti-oxidants, UV absorbers, anti-irritants, anti-microbial agents, dyes and color ingredients, or structuring agents, or any combination thereof.

In other aspects of the present invention, there is disclosed a method of treating a skin condition, comprising topically applying an effective amount of a composition of the present invention to skin. Topical application of the composition can treat or prevent such a skin condition. The effectiveness of the composition can be compared with skin that has not been treated with a composition of the present invention. In certain non-limiting embodiments, the skin treatment can be localized to and/or around an area where the composition is applied to the skin. The skin can be facial, torso, back, neck, ear, pelvic, arms, hands, legs (e.g., ankle, knee, thigh), feet, or buttocks skin. For instance, topical application of a composition to, wherein topical application of the composition treats the skin condition. Non-limiting examples of skin conditions that can be treated or prevented with compositions of the present invention include telangiectasia (i.e., spider veins), eye circles (e.g., dark circles under the eye), puffy eyes, pruritus, lentigo, age spots, senile purpura, keratosis, melasma, blotches, wrinkles, fine lines, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, or hyperpigmentation. In certain aspects, the skin condition can be caused by exposure to UV light, age, irradiation, chronic sun exposure, environmental pollutants, air pollution, wind, cold, heat, chemicals, disease pathologies, or smoking. The skin to be treated can be aged, nutritionally compromised, or environmentally damaged skin. In certain aspects, the composition can be topically applied in an amount effective to increase the stratum corneum turnover rate of the skin, collagen synthesis production of the skin, fat production of the skin, firmness of the skin, or elasticity of the skin. In other aspects, the composition can be topically applied in an amount effective to reduce or inhibit new capillary formation in or near the skin, blood flow to the skin, fluid amount in or near the skin, or melanin production in the skin.

Also disclosed are kits that can include a composition of the present invention. In certain non-limiting aspects, the composition is comprised in a container. The container can be a bottle, dispenser, package, etc. The container can be configured to dispense a pre-determined amount of the composition. The container can be configured to dispense the composition in a semi-solid, liquid, spray, or an aerosol form. In certain aspects, the kit can include indicial on its surface and/or instructions for using the composition.

In other aspects of the present invention, the composition can be used as part of a regimen to treat a skin condition. For instance, the regimen can include applying a composition of the present invention in a first instance as disclosed throughout this specification. The regimen can then include additional applications that are identical, similar, or different than the first instance application. The additional applications can include, for example, a second, third, fourth, fifth, sixth, seventh, eighth, nine, tenth, or more applications with a composition of the present invention and/or whether another method for treating a particular skin condition (e.g., other compositions, surgeries, etc.).

It is contemplated that any embodiment discussed in this specification can be implemented with respect to any method or composition of the invention, and vice versa. Furthermore, compositions of the invention can be used to achieve methods of the invention.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The terms "about" or "approximately" are defined as being close to as understood by one of ordinary skill in the art, and in one non-limiting embodiment the terms are defined to be within 10%, within 5%, within 1%, and in certain aspects within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

In today's image conscious society, people are continually looking for a product that can improve the visual appearance of their skin. The skin's appearance can be affected in a negative way from skin conditions. For instance, spider veins (i.e., telangiectasias or sunburst varicosities) can appear on a person's skin (e.g., face, thighs, calves, ankles, arms, torso, buttocks, etc.) as unsightly clusters of red, blue or purple veins. Under eye circles and puffy eyes can appear as dark circles and swelling around the periorbital area, respectively. Additionally, aged or environmentally damaged skin which can include the appearance fine lines and wrinkles, loss of elasticity, increased sagging, loss of firmness, loss of color evenness or tone, coarse surface texture, and mottled pigmentation.

In one aspect, the present invention provides compositions and methods for treating skin conditions. In one non-limiting embodiment, the compositions of the present invention can be used to treat spider veins, eye circles, puffy eyes, or environmentally damaged skin by topically applying a composition of the present invention to an area of the skin that needs such treatment. As noted throughout this specification, the compositions can include at least one or any combination of the following ingredients: *Magnolia* extract; honokiol, magnolol, *humulus lupulus* extract, hesperidin methyl chalcone, gotu kola, dipeptide valyl-tryptophane, palmitoyl tetrapeptide-3, *corylus avellana* bud extract, *cucumis sativa* extract, *morus alba* extract, *hibiscus sabdariffa* flower extract, *vitis vinifera* extract, ascorbyl glucoside, *citrus medica limonum* extract, *avena sativa* kernel extract, hydrolyzed soy protein, aniseed myrtle extract, *tasmania lanceolata* leaf extract, *artemisia abrotanum* extract, *citrus grandis* fruit extract, or apigenin. These and other non-limiting aspects of the present invention are described in further detail in the following sections.

A. Ingredients

The following subsections provide non-limiting examples of ingredients that can be included into compositions of the present invention. The compositions can include any one of the following ingredients or a combination of such ingredients. It is contemplated that other ingredients can also be incorporated into the compositions. Further, a person of ordinary skill in the art would recognize that the ingredients are commercially available, can be chemically synthesized, or can be isolated or purified by known methods from sources that includes such ingredients.

1. *Magnolia* Extract

In certain non-limiting embodiments, the compositions of the present invention can include a *Magnolia* extract. The *Magnolia* extract can be obtained or derived from a variety of sources from a *Magnolia* plant (e.g., flower, bark, seed cone, etc.). In general, *Magnolia* is a large genus of about 210 flowering plant species in the subfamily Magnoliodieae of the family Magnoliaceae. *Magnolia* extract can be obtained from the species within the Magnoliaceae family. Non-limiting examples of these species include *Magnolia acuminata, Magnolia ashei, Magnolia biondii, Magnolia cylindrica, Magnolia cambellii, Magnolia denudata, Magnolia fraseri, Magnolia grandiflora, Magnolia hypoleuca, Magnolia kobus, Magnolia hliiflora, Magnolia loegneri, Magnolia macrophylla, Magnolia officinalis, Magnolia pyramidata, Magnolia sargentiana, Magnolia seiboldii, Magnolia soulangiana, Magnolia sprengeri, Magnolia stellata, Magnolia tripetala, Magnolia virginiana, Magnolia zenii*, and *Michelia figo*. A more complete listing of the species within the Magnoliaceae family can be found in Figlar & Nooteboom (2004), which is incorporated by reference.

*Magnolia* extract can reduce the blood flow near the skin surface though a variety of ways (e.g., vasoconstriction, inhibition of angiogenesis, endothelial cell migration, or tube formation in or near the skin area that has been contacted with a composition containing *Magnolia* extract). Active ingredients that have been identified in *Magnolia* flower, bark, and seed cone extracts include magnolol, dihydroxydihdromagnolol, honokiol, and dihydrohonokiol. These are polyphenolic containing compounds in which honokiol is an isomer of magnolol.

*Magnolia* extracts are commercial available from a variety of different sources. For instance *Magnolia* extracts can be purchased from Carrubba, Inc. (Milford Conn.), Arcadia Herbs & Alternatives (Langhorne, Pa.), and Herbal Extracts Plus (Croydon, Pa.). Alternatively, a person of ordinary skill in the art would be able to isolate *Magnolia* extract from the *Magnolia* flower, bark, or seed cone by using any suitable isolation and purification methods known in the art (see e.g., Bai et al. (2003).

2. Honokiol and Magnolol

The compositions of the present invention can include honokiol or magnolol or both. As noted above, these are biphenolic containing compounds in which honokiol is an isomer of magnolol. These compounds can be useful in reducing the blood flow near the skin surface through a variety of mechanisms (e.g., vasoconstriction, inhibition of angiogenesis, endothelial cell migration, or tube formation in or near the skin area that has been contacted with a composition containing honokiol or magnolol). The chemical structures of these compounds are illustrated below:

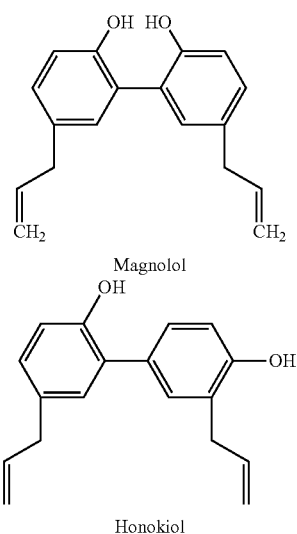

Honokiol and magnolol can be isolated or purified from *Magnolia* extracts (e.g., flower, bark, and seed cone extracts) or other extracts that include such compounds by standard techniques. Alternatively, these compounds are commercially available (e.g., Wako Chemical Company (Tokyo, Japan)) or can be synthesized using convention chemical synthesis techniques known to those of ordinary skill in the art (see, e.g., Vollhardt and Schore, 1994).

3. Chemical Compounds and Extracts

The compositions of the present invention can include *humulus lupulus* extract, gotu kola (*centella asiatica* extract), hesperidin methyl chalcone, dipeptide valyl-tryptophane, palmitoyl tetrapeptide-3, *corylus avellana* bud extract, *cucumis sativa* extract, *morus alba* extract, *hibiscus sabdariffa* flower extract, *vitis vinifera* extract, ascorbyl glucoside, *citrus medica limonum* extract, *avena sativa* kernel extract, hydrolyzed soy protein, aniseed myrtle extract, *tasmania lanceolata* leaf extract, *artemisia abrotanum* extract, *citrus grandis* fruit extract, or apigenin or any combination or mixture of such ingredients.

For instance, *Humulus lupulus* extract, or hops extract, can be used to reduce blood flow near the skin surface though the vasoconstriction, inhibition of angiogenesis, inhibition of endothelial cell migration or tube formation in or near the skin area that has been contacted with a composition containing hops extract. Hops extract is commercially available through a variety of sources (e.g., Actives International (Allendale, N.J.)) and can also be isolated or purified from *Humulus lupulus* plants by standard isolation and purification techniques. Non-limiting examples of varieties of *Humulus lupulus* from which hops extract can be obtained include *Humulus lupulus* var. *lupulus, Humulus lupulus* var. *cordifolius, Humulus lupulus* var. *lupuloides* (syn. *H. americanus*), *Humulus lupulus* var. *neomexicanus*, and *Humulus lupulus* var. *pubes-*

*cens. Humulus lupulus* extract includes active ingredients such as humulene and lupulene.

Gotu kola (*Centella asiatica*) extract is a vine-like plant that is native to India and Southeast Asia. This ingredient can be used to strengthen capillary micro vessel barrier which can improve the overall function of blood vessels (e.g., efficient or improved blood circulation) in or near the skin area that has been contacted with a composition containing Gotu kola extract. Gotu kola extract is commercially available through a variety of sources (e.g., Naturex (South Hackensack, N.J.)) and can also be isolated or purified from Gotu kola containing plants by standard isolation and purification techniques. Gotu kola extract contains active ingredients such as asiaticoside (a triterpene glycoside) (triterpenoid), brahmoside and brahminoside (both saponin glycosides), madecassoside (a glycoside with anti-inflammatory properties), madecassic acid, thiamine, riboflavin, pyridoxine, vitamin K, asparate, glutamate, serine, threonine, alanine, lysine, histidine, magnesium, calcium and sodium.

Hesperidin methyl chalcone, dipeptide valyl-tryptophane (i.e., dipeptide-2 which comprises valine and tryptophan), and palmitoyl tetrapeptide-3 (which is the reaction product of palmitic acid and a synthetic peptide containing glycine, glutamine, proline, and arginine) can also be included in compositions of the present invention. Hesperidin, a bioflavonoid which can be found in citrus peel such as the peel of sweet oranges (*Citrus aurantium* var. *sinensis*), can be converted into hesperidin methyl chalcone by extracting hesperidin from its source and placing the extract into an alkaline solution. This converts hesperidin into hesperidin chalcone which can subsequently be methylated by any known methylation process to produce hesperidin methyl chalcone. Hesperidin methyl chalcone can strengthen capillary micro vessel barrier in or near skin area that has been contacted with a composition including this ingredient. Dipetide valyl-tryptophane, which is commercially available under the trade name DIPEPTIDE VW™ through Sederma SAS (Cedex, France), can be used to mobilize fluid in skin tissue and drain the fluid from such tissue (which can reduce puffy eyes) when applied to the skin. Palmitoyl tetrapeptide-3, which is commercially available under the trade name N-PALMITOYL RIGIN™ through Sederma SAS (Cedex, France), can reduce local inflammation in skin tissue and restore skin firmness and elasticity when applied to skin. Further, a blend of these three ingredients is also commercially available under the trade name EYELISS™ through Dermaxime (Gauteng, South Africa).

*Corylus* (Hazel) extract can moisturize skin and can be used to mobilize fluid in skin tissue and drain the fluid from such tissue (which can reduce puffy eyes) when applied to the skin. The extract can be obtained from the bud, flower, leaves, nut, bark, etc. from the Hazel plant. Hazel extract is commercially available through a variety of sources (e.g., Mountain Rose Herbs, Eugene Oreg.) and can also be isolated or purified from Hazel plants by standard isolation and purification techniques. Non-limiting examples of species of which Hazel extract can be obtained include *Corylus americana, Corylus avellana, Corylus chinensis, Corylus colurna, Corylus cornuta, Corylus ferox, Corylus heterophylla, Corylus jacquemontii, Corylus maxima, Corylus sieboldiana*, and *Corylus tibetica*.

*Cucumis sativa* (Cucumber) extract, *morus alba* extract, *hibiscus sabdariffa* flower extract, and *vitis vinifera* extract can be used in to brighten or even skin tone by inhibiting tyrosinase activity when applied to the skin. These ingredients are commercially available through a variety of sources and can also be isolated or purified from plants containing these extracts by standard isolation and purification techniques. In certain non limiting aspects, a blend of these ingredients can be used to obtain brighter or more even skin tone. Such a blend is commercially available under the trade name CLERILYS™ through GreenTech SA (Saint Beauzire, France).

Ascorbyl glucoside can also be used to brighten or even skin tone by inhibiting tyrosinase activity when applied to the skin. Ascorbyl glucoside is a derivative of ascorbic acid (vitamin C) that includes an attached glucose sugar. In an ascorbyl glucoside molecule, typically, the glucose is typically attached at an OH group of ascorbic acid. The following is a non-limiting example of one form of ascorbyl glucoside, ascorbic acid-2 glucoside:

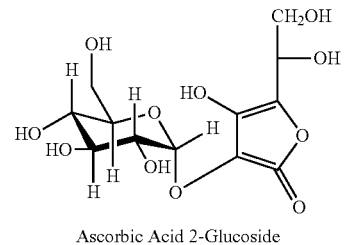

Ascorbic Acid 2-Glucoside

Other non-limiting examples of ascorbyl glucoside include ascorbic acid 1-glucoside (including 1-O-α-D-glucopyranosyl-L-ascorbic acid and 1-O-β-D-glucopyranosyl-L-ascorbic acid), ascorbic acid 2-glucoside (including 2-O-α-D-glucopyranosyl-L-ascorbic acid and 2-O-β-D-glucopyranosyl-L-ascorbic acid), ascorbic acid 3-glucoside (including 3-O-α-D-glucopyranosyl-L-ascorbic acid or 3-O-β-D-glucopyranosyl-L-ascorbic acid), ascorbic acid 5-glucoside (including 5-O-α-D-glucopyranosyl-L-ascorbic acid or 5-O-β-D-glucopyranosyl-L-ascorbic acid), and ascorbic acid 6-glucoside (including 6-O-α-D-glucopyranosyl-L-ascorbic acid or 6-O-β-D-glucopyranosyl-L-ascorbic acid). Ascorbyl glucoside is commercially available (e.g., Hayashibara Biochemical Laboratories, Inc.). The preparation of ascorbyl glucoside is also known in the art (see, e.g. U.S. Pat. Nos. 5,084,563; 5,252,722; 5,272,136; 5,388,420; 5,432,161; 5,843,907; and 5,508,391).

The compositions of the present invention can include an extract formulation comprising *cucumis sativa* (Cucumber) extract and *citrus medica limonum* (Lemon). Such a formulation can be used to brighten or even skin tone by inhibiting tyrosinase activity when applied to the skin. Such a formulation is commercially available under the trade name UNINONTAN U34™ through Chesham Chemicals, Ltd. (United Kingdom). Ingredients with the UNINONTAN U34™ formulation include cucumber extract (*cucumis sativus*) (15.0%), lemon extract (*citrus medica limonum*) (16.0%), sodium citrate (20.0%), propylene glycol (23.5%), and water (25.5%).

Non-limiting examples of anti-irritants and anti-oxidants that can be included in the compositions of the present invention include *Avena sativa* (Oat) extract, hydrolyzed soy protein, aniseed myrtle extract, *tasmania lanceolata* leaf extract, and *Hibiscus sabdariffa* (roselle) flower extract, or any combination or mixture of such ingredients. These ingredients are commercially available through a variety of sources and can also be isolated or purified from plants containing these extracts by standard isolation and purification techniques. For instance, a composition comprising Oat extract is commercially available under the trade name DRAGO CALM™ through Symrise (Holzminden, Germany). Hydrolyzed soy protein is commercially available under the trade name AQUA PRO SP™ through MGP Ingredients, Inc. (Atchison, Kans.). A blend of *Anetholea anisata* (aniseed myrtle) extract, *Tasmania lanceolota* (tasmanian mountain pepperberry) leaf extract, and *Hibiscus sabdariffa* (roselle) flower extract is commercially available under the trade name MOUNTAIN HARVEST™ through Southern Cross Botanicals (Knockrow, Australia).

*Artemisia abrotanum* (Southernwood) extract can stimulate adipogenesis and aid in the protection of the fat pad under the eye. This can be beneficial in combating fine lines and wrinkles and thinning/slackening skin. Southernwood extract is commercially available under the trade name PULPACTYL™ through Silab (Cedex, France) and can also be isolated or purified from plants containing these extracts by standard isolation and purification techniques.

*Citrus grandis* (Grapefruit) peel extract has anti-hyaluronidase, anti-angiogenesis, anti- and inflammatory properties when applied to skin. This ingredient can be used as a soothing agent for acute or chronic inflammation and can help repair skin damaged from excessive UV exposure. An active ingredient in Grapefruit extract is Apigenin. Grapefruit extract is commercially available under the trade name VIAPURE CITRUS™ through Actives International (Allendale, N.J.) and can also be isolated or purified from plants containing these extracts by standard isolation and purification techniques.

4. Cosmetic Ingredients

Compositions of the present invention can include other ingredients. Non-limiting examples of additional ingredients that can be added to cosmetic formulations can be found in the International Cosmetic Ingredient Dictionary, 10th Ed., 2004, which is incorporated by reference. Such ingredients include surfactants, preservatives, absorbents, adsorbents, chelating agents, lubricants, solvents, moisturizers (including, e.g., emollients, humectants, film formers, occlusive agents, and agents that affect the natural moisturization mechanisms of the skin), water repellents, anti-oxidants, UV absorbers, anti-irritants, vitamins, trace metals, anti-microbial agents, dyes and color ingredients, and/or structuring agents (see, e.g., McCutcheon's Functional Materials North American Edition 2001 and McCutcheon's Emulsifiers & Detergents North American Edition 2001; U.S. Pat. No. 6,290,938).

a. Surfactants

The compositions of the present invention can also comprise one or more surfactants. Surfactants can reduce the in interfacial tension between phases and improve the formulation and stability of a formulation. The surfactants can be nonionic, cationic, anionic, cryptoanionic, and zwitterionic emulsifiers (See McCutcheon's Emulsifiers & Detergents (2001); U.S. Pat. Nos. 5,011,681; 4,421,769; 3,755,560, 6,117,915). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, cetyl phosphate, potassium cetyl phosphate, diethanolamine cetyl phosphate, polysorbate 20, polysorbate 60, polysorbate 80, glyceryl stearate, PEG-100 stearate, tyloxapol, and mixtures thereof.

b. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

c. Moisturizers

Non-limiting examples of moisturizers include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, *aloe barbadensis, aloe-barbadensis* extract, *aloe barbadensis* gel, *althea officinalis* extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *eucalyptus globulus* oil, evening primrose (*oenothera biennis*) oil, fatty acids, fructose, gelatin, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites molucana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

d. Emollients

Examples of emollients include, but are not limited to, vegetable oils, mineral oils, silicone oils, synthetic and natural waxes, medium chain triglycerides, petrolatum, lanolin, aluminum magnesium hydroxide stearate (which can also function as a water repellent), and fatty acid esters. Non-limiting examples of vegetable oils include safflower oil, corn oil, sunflower seed oil, and olive oil.

e. Antioxidants

Examples of antioxidants include, but are not limited to, acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

f. Compounds Having Ultraviolet Light Absorbing Properties

Non-limiting examples of compounds that have ultraviolet light absorbing properties that can be used with the compounds of the present invention include benzophenone, benzophenone-1, benzophenone-2, benzophenone-3, benzophenone-4 benzophenone-5, benzophenone-6, benzophenone-7, benzophenone-8, benzophenone-9, benzophenone-10, benzophenone-11, benzophenone-12, benzyl salicylate, butyl PABA, cinnamate esters, cinoxate, DEA-methoxycinnamate, diisopropyl methyl cinnamate, ethyl dihydroxypropyl PABA, ethyl diisopropylcinnamate, ethyl methoxycinnamate, ethyl PABA, ethyl urocanate, glyceryl octanoate dimethoxycinnamate, glyceryl PABA, glycol salicylate, homosalate, isoamyl p-methoxycinnamate, PABA, PABA esters, Parsol 1789, isopropylbenzyl salicylate, and octyl methoxycinnamate.

g. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. Other non-limiting examples can be found in International Cosmetic Ingredient Dictionary, 10th edition, 2004, which is incorporated by reference.

h. Silicone Containing Compounds

In non-limiting aspects, silicone containing compounds include any member of a family of polymeric products whose molecular backbone is made up of alternating silicon and oxygen atoms with side groups attached to the silicon atoms.

By varying the —Si—O— chain lengths, side groups, and cross linking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e., dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in International Cosmetic Ingredient Dictionary, 10th edition, 2004, which is incorporated by reference as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

i. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

j. Thickening Agents

Thickening agents, including thickener or gelling agents, include substances which that can increase the viscosity of a composition. Certain thickeners can increase the viscosity of a composition without substantially modifying the efficacy of the active ingredient within the composition. Thickeners can also increase the stability of the compositions of the present invention.

Non-limiting examples of thickening agents that can be used in the context of the present invention include hydrogenated polyisobutene or trihydroxystearin or combination of both. Other examples include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Tenth Edition, 2004). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379.

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (e.g., hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

k. Additional Ingredients

Non-limiting examples of additional compounds and agents that can be used with the compositions of the present invention include, vitamins (e.g., D, E, A, K, and C), trace metals (e.g., zinc, calcium and selenium), anti-irritants (e.g., steroids and non-steroidal anti-inflammatories), botanical extracts (e.g. aloe vera, chamomile, cucumber extract, *ginkgo biloba*, ginseng, and rosemary), dyes and color ingredients (e.g., D&C blue no. 4, D&C green no. 5, D&C orange no. 4, D&C red no. 17, D&C red no. 33, D&C violet no. 2, D&C yellow no. 10, D&C yellow no. 11 and DEA-cetyl phosphate), emollients (i.e., organic esters, fatty acids, lanolin and its derivatives, plant and animal oils and fats, and di- and triglycerides), antimicrobial agents (e.g., triclosan and ethanol), and fragrances (natural and artificial).

B. Source of Ingredients

The ingredients of the compositions of the present invention can be obtained by any means known to a person of ordinary skill in the art. In a non-limiting embodiment, for example, the ingredients can be isolated by obtaining the source of such ingredient. In many instances, the ingredients are also commercially available as explained above. For example, *Magnolia* extracts can be obtained through any number of companies including Carrubba, Inc. (Milford Conn.), Arcadia Herbs & Alternatives (Langhorne, Pa.), and Herbal Extracts Plus (Croydon, Pa.). Additionally, the compounds, agents, and active ingredients can be purified by any number of techniques known to a person of ordinary skill in the art. Non-limiting examples of purification techniques include Polyacrylamide Gel Electrophoresis, High Performance Liquid Chromatography (HPLC), Gel chromatography or Molecular Sieve Chromatography, and Affinity Chromatography. In other aspects, the compounds, agents, and active ingredients can be obtained by chemical synthesis or by recombinant means by using conventional techniques. See, for example, Stewart and Young, (1984); Tam et al., (1983); Merrifield, (1986); and Barany and Merrifield (1979), Houghten (1985).

C. Modifications and Derivatives

Modifications or derivatives of the ingredients disclosed throughout this specification are also contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. Such derivatives may have the addition, removal, or substitution of one or more chemical moieties on the parent molecule. Non limiting examples of the types modifications that can be made to the compounds and structures disclosed throughout this document include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, hetero atoms such as N, S, or O can be substituted into the structure instead of a carbon atom.

D. Equivalents

Known and unknown equivalents to the ingredients discussed throughout this specification and claims can be used with the compositions and methods of the present invention. The equivalents can be used as substitutes for any given ingredient in a composition of the present invention. The equivalents can also be used to add to the methods and compositions of the present invention. A person of ordinary skill in the art would be able to recognize and identify acceptable known and unknown equivalents to the ingredients without undue experimentation.

E. Compositions of the Present Invention

A person of ordinary skill would recognize that the compositions of the present invention can include any number of combinations of the ingredients discussed throughout this specification. It is also contemplated that that the concentrations of the ingredients can vary. In non-limiting embodiments, for example, the compositions may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the ingredients mentioned throughout the specification and claims. In non-limiting aspects, the percentage can be calculated by weight or volume of the total composition. A person of ordinary skill in the art would understand that the concentrations can vary depending on the desired effect of the composition and/or on the product into which the composition is incorporated into.

F. Cosmetic Vehicles

The compositions of the present invention can be incorporated in a variety of different vehicles. Non-limiting examples of suitable vehicles include emulsions (e.g., oil/water emulsion, an oil/water/oil emulsion, a water/oil emulsion, a water/oil/water emulsion, a water/silicone emulsion, a water/silicone/water emulsion, a silicone/water emulsion, a silicone/water/silicone emulsion, a water/wax emulsion, or an oil/water/silicone emulsion), creams, lotions, solutions (both aqueous and hydro-alcoholic), anhydrous bases (e.g., lipsticks and powders), gels, ointments, serums, liquids, fluids, non-aerosol sprays, aerosol sprays, non-aerosol foams, aerosol foams or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of ingredients be selected in such a way that the combinations are chemically compatible and do not form complexes which precipitate from the finished product.

G. Cosmetic Products

The composition of the present invention can also be used in many cosmetic products including, but not limited to, concealers, foundations, sunscreen products, sunless skin tanning products, moisturizing creams, skin benefit creams and lotions, softeners, day lotions, gels, ointments, night creams, lipsticks, cleansers, toners, masks, hair products, finger nail products, and other known cosmetic products or applications.

H. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions (e.g., foundations), or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other dispersions or compositions included in the container. Instructions can include an explanation of how to apply, use, and maintain the products, dispersions, or compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

A non-limiting example of a composition of the present invention is described in Table 1. This composition is a cream that can be topically applied to skin.

TABLE 1*

| Phase | Ingredient | % Concentration by weight |
|---|---|---|
| A | Water | 66.70 |
|  | Disodium EDTA | 0.10 |
|  | Dimethicone | 1.00 |
|  | Butylene glycol | 1.50 |
| B | Polysorbate-20 | 0.50 |
|  | Menthyl lactate | 0.20 |
| C | HDI/trimethylol hexyllactone C | 5.00 |
|  | Polyacrylamide C13-14 Isopr | 2.25 |
|  | Silicone HL88 | 1.00 |
|  | Hispagel Oil/LV | 4.00 |
| D | Ascorbyl glucoside | 0.10 |
|  | Clerilys | 0.50 |
|  | Sodium citrate and lemon extract | 0.10 |
|  | *Magnolia biondii* flower extract | 2.00 |
|  | Mountain Harvest ™ | 0.50 |
|  | Hydrolyzed soy protein | 2.00 |
|  | *Centella asiatica* extract | 1.00 |
|  | *Citrus grandis* (grapefruit) peel | 0.50 |
|  | *Humulus lupulus* (hops) extract | 0.50 |
|  | Eyeliss | 1.50 |
|  | *Corylus avellana* (hazel) bud extract | 1.00 |
|  | Dermochlorella D | 1.00 |
|  | *Avena sativa* (oat) kernal extract | 1.50 |
|  | *Artemisia abrotanum* extract | 4.00 |
| E | Diazolidinyl urea | 0.20 |
|  | Iodo propynyl butylcarbamate | 0.10 |
|  | Natural extract blend 33137* | 0.25 |
|  | Total | 100.0 |

*The Natural extract blend contains 6.3% *Citrus Tangerina* (tangerine) extract, 63.7% *Citrus aurantium dulcis* (orange) peel extract, and 30% phenoxyethanol (preservative).

The following non-limiting procedure was used to prepare the composition in Table 1. All Phase A ingredients were added to water in a main vessel and dispersed by propeller and sweep mixing. The mixture was heated to 55-60° C. and while mixing. In a separate vessel, the Phase B ingredients were heated to 55-60° C. or until the solids melted. The Phase B mixture was added to the main vessel and mixed for approximately fifteen (15) minutes. The heat source was removed. The Phase C ingredients were added to the main vessel in the order listed in Table 1 while mixing. Before the Phase D ingredients were added, the mixture resembled a smooth, thick, white cream. The Phase D ingredients were added to the main vessel at approximately 50° C. while mixing (note that the Phase D ingredients can be made into a slurry prior to adding to the main vessel, if needed). As the Phase D ingredients are added, the mixture will thin back down and turn a yellow shade. The Phase E ingredients are then added at 40-45° C. Mixing is continued as the mixture is cooled to 30-35° C.

Example 2

Testing Parameters of the Table 1 Composition: The efficacy of the composition in Table 1 was tested on human skin. The composition was tested on one-hundred and twenty three (123) women ("panelists") having the following characteristics: (a) ½ of the women were between the ages of 32 to 45 and ½ were between 46 to 60 years of age; (b) ⅓ of the women had dry/dry to normal skin, ⅓ had normal skin and ⅓ had combination skin/oily skin; (c) 80% of the women had noticeably mild/moderate "under eye puffiness;" and (d) 50% of the women used a facial concealer product 3 or more times a week. A summary of the panelists' skin conditions is in Table 2. The composition was applied to the under eye skin area twice a day (once in the morning and evening) for a total of fourteen (14) days. The panelists filled out questionnaires that inquired into the tactile properties and efficacy of the composition.

TABLE 2

(Panelist Skin Conditions)

| | | AGE | | SKIN TYPE@ | | | SKIN TONE | | |
|---|---|---|---|---|---|---|---|---|---|
| | Total | 35-45 | 46-60 | Dry | Normal | Oily | Light | Medium | Dark |
| Base: Total Respondents | (123) % | (57) % | (66) % | (41) % | (38) % | (44) % | (49)@ % | (50) % | (24)@ % |
| Crow's Feet | 55 | 37 | 71 | 59 | 61 | 48 | 53 | 60 | 50 |
| Dark Circles | 100 | 100 | 100 | 100 | 100 | 100 | 100 | 100 | 100 |
| Mild | 69 | 83 | 58 | 66 | 66 | 75 | 61 | 74 | 75 |
| Moderate | 31 | 17 | 42 | 34 | 34 | 25 | 39 | 26 | 25 |
| Undereye Puffiness | 85 | 77 | 92 | 85 | 87 | 84 | 84 | 86 | 88 |
| Mild | 64 | 68 | 61 | 63 | 66 | 64 | 55 | 68 | 75 |
| Moderate | 21 | 9 | 31 | 22 | 21 | 20 | 29 | 18 | 13 |

Results of the Table 1 Composition: The panelists' responses are summarized in the following Tables 3-16. The responses in Table 3 concern the tactile properties and efficacy of the composition immediately after application to the skin.

TABLE 3

(Immediately After Application)

| Claim Attribute* | Number of Respondents | % Agree | % Disagree |
|---|---|---|---|
| Is easy to apply | 123 | 98 | 2 |
| Is lightweight | 122 | 98 | 2 |
| Leaves a soft afterfeel | 123 | 96 | 4 |
| My regular eye cream applies easily over the test product | 118 | 96 | 4 |
| My regular foundation applies easily over the test product | 117 | 96 | 4 |
| Does not feel oily/greasy during application | 123 | 93 | 7 |
| Provides a cooling sensation upon application | 119 | 92 | 8 |
| Does not leave an oily/greasy afterfeel | 123 | 91 | 9 |
| Leaves a smooth afterfeel | 121 | 90 | 10 |
| Is suitable for my skin type | 121 | 90 | 10 |
| Has a silky-smooth texture | 121 | 87 | 13 |
| Absorbs quickly | 122 | 84 | 16 |
| Provides a cooling sensation that lasts a few minutes | 122 | 82 | 18 |
| Visibly reduces appearance of undereye puffiness immediately after application | 115 | 56 | 44 |
| Visibly minimizes appearance of undereye puffiness immediately after application | 115 | 50 | 50 |
| Visibly minimizes appearance of dark circles immediately after application | 118 | 49 | 51 |
| Visibly reduces appearance of dark circles immediately after application | 117 | 44 | 56 |

*Excluding "does not apply to me/don't know"

The panelists' responses in Table 4 concern the efficacy of the composition after two weeks of use.

TABLE 4

(After Two Weeks of Use)

| Claim Attribute* | Number of Respondents | % Agree | % Disagree |
|---|---|---|---|
| Freshens my eye area | 121 | 88 | 12 |
| Softens appearance of undereye puffiness | 115 | 80 | 20 |
| Rejuvenates eye area | 120 | 78 | 22 |
| Visibly minimizes appearance of undereye puffiness | 112 | 75 | 25 |
| Leaves eye area with a rested look | 119 | 75 | 25 |
| Softens appearance of dark circles | 118 | 74 | 26 |
| Improves appearance of undereye puffiness | 114 | 74 | 26 |
| Visibly reduces appearance of undereye puffiness | 113 | 73 | 27 |
| Revitalizes eye area | 122 | 73 | 27 |
| Diminishes appearance of undereye puffiness | 112 | 70 | 30 |
| Softens appearance of undereye sagginess | 102 | 70 | 30 |
| Visibly minimizes appearance of dark circles | 118 | 69 | 31 |
| Leaves eye area looking younger | 121 | 69 | 31 |
| Improves appearance of dark circles | 118 | 68 | 32 |
| Brightens up eye area | 121 | 68 | 32 |
| Visibly reduces appearance of dark circles | 117 | 66 | 34 |
| Improves appearance of undereye sagginess | 103 | 66 | 34 |
| Leaves eye area looking vibrant | 120 | 66 | 34 |
| Diminishes appearance of dark circles | 118 | 64 | 36 |
| Visibly reduces appearance of undereye sagginess | 102 | 63 | 37 |

TABLE 4-continued (After Two Weeks of Use)

| Claim Attribute* | Number of Respondents | % Agree | % Disagree |
|---|---|---|---|
| Visibly minimizes appearance of undereye sagginess | 102 | 61 | 39 |
| Diminishes appearance of undereye sagginess | 103 | 56 | 44 |

The responses in Table 5 concern the tactile properties and efficacy of the composition immediately after application to the skin. The responses are organized by panelist age.

TABLE 5

(Age--Immediately After Application)

| | AGE | |
|---|---|---|
| Immediately After Application - "% Agree" | 32-45 % | 46-60 % |
| Is easy to apply | 97 | 99 |
| Is lightweight | 96 | 99 |
| Leaves a soft afterfeel | 93 | 99 |
| My regular eye cream applies easily over the test product | 93 | 98 |
| My regular foundation applies easily over the test product | 91 | 100 |
| Does not feel oily/greasy during application | 90 | 96 |
| Provides a cooling sensation upon application | 91 | 94 |
| Does not leave an oily/greasy afterfeel | 90 | 92 |
| Leaves a smooth afterfeel | 88 | 92 |
| Is suitable for my skin type | 90 | 91 |
| Has a silky-smooth texture | 91 | 83 |
| Absorbs quickly | 84 | 85 |
| Provides a cooling sensation that lasts a few minutes | 73 | 89 |
| Visibly reduces appearance of undereye puffiness immediately after application | 55 | 57 |
| Visibly minimizes appearance of undereye puffiness immediately after application | 48 | 51 |
| Visibly minimizes appearance of dark circles immediately after application | 45 | 53 |
| Visibly reduces appearance of dark circles immediately after application | 38 | 49 |

The panelists' responses in Table 6 concern the efficacy of the composition after two weeks of use. The responses are organized by panelist age.

TABLE 6

(Age--After Two Weeks of Use)

| | AGE | |
|---|---|---|
| Two Weeks After Use - "% Agree" | 32-45 % | 46-60 % |
| Dark Circles | | |
| Visibly minimizes appearance of dark circles | 73 | 65 |
| Improves appearance of dark circles | 67 | 68 |
| Visibly reduces appearance of dark circles | 66 | 66 |
| Diminishes appearance of dark circles | 71 | 59 |
| Softens appearance of dark circles | 80 | 68 |
| Puffiness | | |
| Softens appearance of undereye puffiness | 83 | 77 |
| Visibly minimizes appearance of undereye puffiness | 73 | 77 |
| Improves appearance of undereye puffiness | 77 | 71 |
| Visibly reduces appearance of undereye puffiness | 74 | 72 |
| Diminishes appearance of undereye puffiness | 71 | 69 |
| Saggy Skin | | |
| Softens appearance of undereye sagginess | 71 | 68 |
| Improves appearance of undereye sagginess | 63 | 68 |

TABLE 6-continued (Age--After Two Weeks of Use)

| | AGE | |
|---|---|---|
| Two Weeks After Use - "% Agree" | 32-45 % | 46-60 % |
| Visibly reduces appearance of undereye sagginess | 59 | 66 |
| Visibly minimizes appearance of undereye sagginess | 59 | 63 |
| Diminishes appearance of undereye sagginess | 52 | 60 |
| General Appearance Of Eye Area | | |
| Freshens my eye area | 87 | 89 |
| Rejuvenates eye area | 84 | 72 |
| Leaves eye area with a rested look | 76 | 73 |
| Revitalizes eye area | 75 | 71 |
| Leaves eye area looking younger | 75 | 63 |
| Brightens up eye area | 71 | 65 |
| Leaves eye area looking vibrant | 68 | 64 |

The panelists' responses in Table 7 concern the tactile properties and efficacy of the composition immediately after application to the skin. The responses are organized by panelists who have mild/moderate under eye puffiness and panelists who do not have under eye puffiness.

TABLE 7

(Under Eye Puffiness--Immediately After Application)

| | UNDEREYE PUFFINESS | |
|---|---|---|
| Immediately After Application - "% Agree" | Have Mild/ Moderate Undereye Puffiness % | Do Not Have Undereye Puffiness % |
| Is easy to apply | 97 | 100 |
| Is lightweight | 98 | 94 |
| Leaves a soft afterfeel | 96 | 94 |
| My regular eye cream applies easily over the test product | 97 | 88 |
| My regular foundation applies easily over the test product | 97 | 89 |
| Does not feel oily/greasy during application | 94 | 89 |
| Provides a cooling sensation upon application | 92 | 94 |
| Does not leave an oily/greasy afterfeel | 92 | 83 |
| Leaves a smooth afterfeel | 90 | 89 |
| Is suitable for my skin type | 90 | 89 |
| Has a silky-smooth texture | 85 | 100 |
| Absorbs quickly | 85 | 83 |
| Provides a cooling sensation that lasts a few minutes | 85 | 65 |
| Visibly reduces appearance of undereye puffiness immediately after application | 58 | 41 |
| Visibly minimizes appearance of undereye puffiness immediately after application | 52 | 33 |
| Visibly minimizes appearance of dark circles immediately after application | 49 | 50 |
| Visibly reduces appearance of dark circles immediately after application | 44 | 39 |

The panelists' responses in Table 8 concern the efficacy of the composition after two weeks of use. The responses are organized by panelists who have mild/moderate under eye puffiness and panelists who do not have under eye puffiness.

TABLE 8

(Undereye Puffiness--After Two Weeks of Use)

| Two Weeks After Use - "% Agree" | UNDEREYE PUFFINESS | |
|---|---|---|
| | Have Mild/Moderate Undereye Puffiness % | Do Not Have Undereye Puffiness % |
| Dark Circles | | |
| Visibly minimizes appearance of dark circles | 66 | 83 |
| Improves appearance of dark circles | 65 | 83 |
| Visibly reduces appearance of dark circles | 64 | 78 |
| Diminishes appearance of dark circles | 63 | 72 |
| Softens appearance of dark circles | 71 | 89 |
| Puffiness | | |
| Softens appearance of undereye puffiness | 78 | 93 |
| Visibly minimizes appearance of undereye puffiness | 72 | 93 |
| Improves appearance of undereye puffiness | 72 | 87 |
| Visibly reduces appearance of undereye puffiness | 69 | 93 |
| Diminishes appearance of undereye puffiness | 68 | 80 |
| Saggy Skin | | |
| Softens appearance of undereye sagginess | 68 | 83 |
| Improves appearance of undereye sagginess | 63 | 85 |
| Visibly reduces appearance of undereye sagginess | 60 | 85 |
| Visibly minimizes appearance of undereye sagginess | 57 | 85 |
| Diminishes appearance of undereye sagginess | 54 | 69 |
| General Appearance Of Eye Area | | |
| Freshens my eye area | 89 | 88 |
| Rejuvenates eye area | 75 | 94 |
| Leaves eye area with a rested look | 74 | 82 |
| Revitalizes eye area | 70 | 89 |
| Leaves eye area looking younger | 66 | 83 |
| Brightens up eye area | 66 | 78 |
| Leaves eye area looking vibrant | 64 | 78 |

The panelists' responses in Table 9 concern the tactile properties and efficacy of the composition immediately after application to the skin. The responses are organized by panelists who have mild dark circles under the eye and panelists who do not have mild dark circles under the eye.

TABLE 9

(Dark Circles--Immediately After Application)

| Immediately After Application - "% Agree" | DARK CIRCLES | |
|---|---|---|
| | Mild % | Moderate % |
| Is easy to apply | 98 | 97 |
| Is lightweight | 98 | 97 |
| Leaves a soft afterfeel | 97 | 95 |
| My regular eye cream applies easily over the test product | 95 | 97 |
| My regular foundation applies easily over the test product | 94 | 100 |
| Does not feel oily/greasy during application | 93 | 92 |
| Provides a cooling sensation upon application | 94 | 90 |
| Does not leave an oily/greasy afterfeel | 89 | 95 |
| Leaves a smooth afterfeel | 93 | 84 |
| Is suitable for my skin type | 91 | 89 |
| Has a silky-smooth texture | 91 | 78 |
| Absorbs quickly | 86 | 82 |
| Provides a cooling sensation that lasts a few minutes | 82 | 82 |
| Visibly reduces appearance of undereye puffiness immediately after application | 60 | 46 |
| Visibly minimizes appearance of undereye puffiness immediately after application | 54 | 39 |
| Visibly minimizes appearance of dark circles immediately after application | 52 | 43 |
| Visibly reduces appearance of dark circles immediately after application | 44 | 42 |

The panelists' responses in Table 10 concern the efficacy of the composition after two weeks of use. The responses are organized by panelists who have mild dark circles under the eye and panelists who do not have mild dark circles under the eye.

TABLE 10

(Dark Circles--After Two Weeks of Use)

| Two Weeks After Use - "% Agree" | DARK CIRCLES | |
|---|---|---|
| | Mild % | Moderate % |
| Dark Circles | | |
| Visibly minimizes appearance of dark circles | 70 | 66 |
| Improves appearance of dark circles | 69 | 66 |
| Visibly reduces appearance of dark circles | 67 | 63 |
| Diminishes appearance of dark circles | 68 | 58 |
| Softens appearance of dark circles | 76 | 68 |
| Puffiness | | |
| Softens appearance of undereye puffiness | 80 | 81 |
| Visibly minimizes appearance of undereye puffiness | 74 | 77 |
| Improves appearance of undereye puffiness | 75 | 71 |
| Visibly reduces appearance of undereye puffiness | 73 | 71 |
| Diminishes appearance of undereye puffiness | 74 | 59 |
| Saggy Skin | | |
| Softens appearance of undereye sagginess | 74 | 60 |
| Improves appearance of undereye sagginess | 69 | 60 |
| Visibly reduces appearance of undereye sagginess | 64 | 60 |
| Visibly minimizes appearance of undereye sagginess | 63 | 57 |
| Diminishes appearance of undereye sagginess | 58 | 53 |
| General Appearance Of Eye Area | | |
| Freshens my eye area | 88 | 90 |
| Rejuvenates eye area | 77 | 78 |
| Leaves eye area with a rested look | 72 | 81 |
| Revitalizes eye area | 74 | 71 |
| Leaves eye area looking younger | 68 | 71 |
| Brightens up eye area | 66 | 71 |
| Leaves eye area looking vibrant | 66 | 65 |

The panelists' responses in Table 11 concern the tactile properties and efficacy of the composition immediately after application to the skin. The responses are organized by panelists who use a concealer product and panelists who do not use a concealer product.

TABLE 11

(Concealer Use--Immediately After Application)

| Immediately After Application - "% Agree" | USE OF CONCEALER | |
|---|---|---|
| | Use Concealer % | Do Not Use Concealer % |
| Is easy to apply | 97 | 98 |
| Is lightweight | 96 | 100 |
| Leaves a soft afterfeel | 94 | 98 |
| My regular eye cream applies easily over the test product | 99 | 92 |
| My regular foundation applies easily over the test product | 99 | 92 |
| Does not feel oily/greasy during application | 94 | 91 |
| Provides a cooling sensation upon application | 89 | 96 |
| Does not leave an oily/greasy afterfeel | 93 | 89 |
| Leaves a smooth afterfeel | 85 | 96 |
| Is suitable for my skin type | 93 | 87 |
| Has a silky-smooth texture | 88 | 85 |
| Absorbs quickly | 84 | 85 |
| Provides a cooling sensation that lasts a few minutes | 81 | 83 |
| Visibly reduces appearance of undereye puffiness immediately after application | 58 | 53 |
| Visibly minimizes appearance of undereye puffiness immediately after application | 52 | 47 |
| Visibly minimizes appearance of dark circles immediately after application | 55 | 42 |
| Visibly reduces appearance of dark circles immediately after application | 47 | 39 |

The panelists' responses in Table 12 concern the efficacy of the composition after two weeks of use. The responses are organized by panelists who use a concealer product and panelists who do not use a concealer product.

TABLE 12

(Concealer Use--After Two Weeks of Use)

| Two Weeks After Use - "% Agree" | USE OF CONCEALER | |
|---|---|---|
| | Use Concealer % | Do Not Use Concealer % |
| Dark Circles | | |
| Visibly minimizes appearance of dark circles | 72 | 65 |
| Improves appearance of dark circles | 72 | 63 |
| Visibly reduces appearance of dark circles | 69 | 62 |
| Diminishes appearance of dark circles | 66 | 63 |
| Softens appearance of dark circles | 78 | 69 |
| Puffiness | | |
| Softens appearance of undereye puffiness | 87 | 71 |
| Visibly minimizes appearance of undereye puffiness | 81 | 67 |
| Improves appearance of undereye puffiness | 79 | 67 |
| Visibly reduces appearance of undereye puffiness | 80 | 63 |
| Diminishes appearance of undereye puffiness | 75 | 62 |
| Saggy Skin | | |
| Softens appearance of undereye sagginess | 78 | 59 |
| Improves appearance of undereye sagginess | 75 | 55 |
| Visibly reduces appearance of undereye sagginess | 71 | 52 |
| Visibly minimizes appearance of undereye sagginess | 69 | 50 |
| Diminishes appearance of undereye sagginess | 66 | 43 |
| General Appearance Of Eye Area | | |
| Freshens my eye area | 91 | 85 |
| Rejuvenates eye area | 82 | 71 |
| Leaves eye area with a rested look | 84 | 64 |
| Revitalizes eye area | 81 | 62 |
| Leaves eye area looking younger | 74 | 62 |
| Brightens up eye area | 75 | 58 |
| Leaves eye area looking vibrant | 72 | 58 |

The panelists' responses in Table 13 concern the tactile properties and efficacy of the composition immediately after application to the skin. The responses are organized by panelists who have dry, normal, and oily skin.

TABLE 13

(Skin Type--Immediately After Application)

| Immediately After Application - "% Agree" | SKIN TYPE | | |
|---|---|---|---|
| | Dry % | Normal % | Oily % |
| Is easy to apply | 100 | 97 | 96 |
| Is lightweight | 95 | 97 | 100 |
| Leaves a soft afterfeel | 98 | 95 | 96 |
| My regular eye cream applies easily over the test product | 95 | 97 | 95 |
| My regular foundation applies easily over the test product | 95 | 97 | 96 |
| Does not feel oily/greasy during application | 95 | 90 | 93 |
| Provides a cooling sensation upon application | 98 | 92 | 88 |
| Does not leave an oily/greasy afterfeel | 90 | 92 | 91 |
| Leaves a smooth afterfeel | 88 | 90 | 93 |
| Is suitable for my skin type | 88 | 94 | 89 |
| Has a silky-smooth texture | 95 | 79 | 86 |
| Absorbs quickly | 85 | 82 | 86 |
| Provides a cooling sensation that lasts a few minutes | 93 | 76 | 77 |
| Visibly reduces appearance of undereye puffiness immediately after application | 58 | 44 | 64 |
| Visibly minimizes appearance of undereye puffiness immediately after application | 63 | 39 | 46 |
| Visibly minimizes appearance of dark circles immediately after application | 55 | 35 | 56 |
| Visibly reduces appearance of dark circles immediately after application | 51 | 37 | 43 |

The panelists' responses in Table 14 concern the efficacy of the composition after two weeks of use. The responses are organized by panelists who have dry, normal, and oily skin.

TABLE 14

(Skin Type--After Two Weeks of Use)

| Two Weeks After Use - "% Agree" | SKIN TYPE | | |
|---|---|---|---|
| | Dry % | Normal % | Oily % |
| Dark Circles | | | |
| Visibly minimizes appearance of dark circles | 63 | 67 | 76 |
| Improves appearance of dark circles | 68 | 64 | 71 |
| Visibly reduces appearance of dark circles | 66 | 58 | 73 |

TABLE 14-continued (Skin Type--After Two Weeks of Use)

| | SKIN TYPE | | |
|---|---|---|---|
| Two Weeks After Use - "% Agree" | Dry % | Normal % | Oily % |
| Diminishes appearance of dark circles | 66 | 53 | 73 |
| Softens appearance of dark circles | 68 | 69 | 83 |
| Puffiness | | | |
| Softens appearance of undereye puffiness | 73 | 80 | 87 |
| Visibly minimizes appearance of undereye puffiness | 70 | 77 | 78 |
| Improves appearance of undereye puffiness | 68 | 80 | 74 |
| Visibly reduces appearance of undereye puffiness | 68 | 77 | 73 |
| Diminishes appearance of undereye puffiness | 68 | 71 | 70 |
| Saggy Skin | | | |
| Softens appearance of undereye sagginess | 64 | 69 | 77 |
| Improves appearance of undereye sagginess | 61 | 69 | 69 |
| Visibly reduces appearance of undereye sagginess | 58 | 66 | 65 |
| Visibly minimizes appearance of undereye sagginess | 58 | 66 | 58 |
| Diminishes appearance of undereye sagginess | 58 | 51 | 59 |
| General Appearance Of Eye Area | | | |
| Freshens my eye area | 85 | 90 | 91 |
| Rejuvenates eye area | 73 | 78 | 81 |
| Leaves eye area with a rested look | 73 | 75 | 76 |
| Revitalizes eye area | 73 | 74 | 72 |
| Leaves eye area looking younger | 59 | 68 | 79 |
| Brightens up eye area | 71 | 61 | 71 |
| Leaves eye area looking vibrant | 63 | 65 | 69 |

The panelists' responses in Table 15 concern the tactile properties and efficacy of the composition immediately after application to the skin. The responses are organized by panelists who have light, medium, and dark skin tones.

TABLE 15

(Skin Tone--Immediately After Application)

| | SKIN TONE* | | |
|---|---|---|---|
| Immediately After Application - "% Agree" | Light % | Medium % | Dark % |
| Is easy to apply | 98 | 96 | 100 |
| Is lightweight | 98 | 96 | 100 |
| Leaves a soft afterfeel | 96 | 94 | 100 |
| My regular eye cream applies easily over the test product | 96 | 98 | 91 |
| My regular foundation applies easily over the test product | 96 | 98 | 91 |
| Does not feel oily/greasy during application | 94 | 94 | 88 |
| Provides a cooling sensation upon application | 96 | 91 | 88 |
| Does not leave an oily/greasy afterfeel | 90 | 94 | 88 |
| Leaves a smooth afterfeel | 88 | 92 | 92 |
| Is suitable for my skin type | 88 | 94 | 88 |
| Has a silky-smooth texture | 85 | 90 | 83 |
| Absorbs quickly | 81 | 88 | 83 |
| Provides a cooling sensation that lasts a few minutes | 86 | 78 | 83 |
| Visibly reduces appearance of undereye puffiness immediately after application | 57 | 52 | 61 |
| Visibly minimizes appearance of undereye puffiness immediately after application | 53 | 50 | 42 |
| Visibly minimizes appearance of dark circles immediately after application | 53 | 47 | 46 |
| Visibly reduces appearance of dark circles immediately after application | 48 | 41 | 42 |

*"Light" = Very Light and Light; "Medium" = Light to Medium, Medium and Medium to Dark; "Dark" = Dark and Very Dark The panelists' responses in Table 16 concern the efficacy of the composition after two weeks of use. The responses are organized by panelists who have light, medium, and dark skin tones.

TABLE 16

(Skin Tone--After Two Weeks of Use)

| | SKIN TONE* | | |
|---|---|---|---|
| Two Weeks After Use - "% Agree" | Light % | Medium % | Dark % |
| Dark Circles | | | |
| Visibly minimizes appearance of dark circles | 65 | 67 | 79 |
| Improves appearance of dark circles | 63 | 71 | 71 |
| Visibly reduces appearance of dark circles | 59 | 70 | 71 |
| Diminishes appearance of dark circles | 63 | 63 | 71 |
| Softens appearance of dark circles | 72 | 73 | 79 |
| Puffiness | | | |
| Softens appearance of undereye puffiness | 71 | 88 | 82 |
| Visibly minimizes appearance of undereye puffiness | 67 | 83 | 73 |
| Improves appearance of undereye puffiness | 66 | 79 | 77 |
| Visibly reduces appearance of undereye puffiness | 66 | 81 | 68 |
| Diminishes appearance of undereye puffiness | 61 | 77 | 71 |
| Saggy Skin | | | |
| Softens appearance of undereye sagginess | 67 | 69 | 76 |
| Improves appearance of undereye sagginess | 67 | 65 | 67 |
| Visibly reduces appearance of undereye sagginess | 59 | 62 | 71 |
| Visibly minimizes appearance of undereye sagginess | 62 | 60 | 62 |
| Diminishes appearance of undereye sagginess | 54 | 58 | 57 |
| General Appearance Of Eye Area | | | |
| Freshens my eye area | 89 | 88 | 88 |
| Rejuvenates eye area | 79 | 78 | 75 |
| Leaves eye area with a rested look | 69 | 76 | 83 |
| Revitalizes eye area | 71 | 76 | 71 |
| Leaves eye area looking younger | 60 | 74 | 75 |
| Brightens up eye area | 60 | 72 | 74 |
| Leaves eye area looking vibrant | 62 | 65 | 75 |

*"Light" = Very Light and Light; "Medium" = Light to Medium, Medium and Medium to Dark; "Dark" = Dark and Very Dark

Example 3

Three ingredients that can be used in the compositions of the present invention were tested to determine their effects on melanin production and tyrosinase activity. The three ingredients were CLERILYS™, Ascorbyl Glucoside, and UNINONTAN U34™. The materials and methods used to perform these tests and the corresponding data follows.

Materials and Methods: Human melanocytes from a moderately pigmented donor were purchased from Cascade Biologics (Portland, Oreg.). Human dermal fibroblasts were purchased from Cambrex (Rockland, Me.). In order to determine the optimal concentrations of the test materials for the whitening experiment, these materials were first examined in a proliferation assay with human dermal fibroblasts. The highest non-interfering concentration was determined for each test material and further 5-fold dilutions were made for use in melanocytes cultures.

The following assay was used to the effects of the materials on melanin production. Melanocytes were seeded in the fully-supplemented 254 medium (Cascade) in 96 well plates and test materials were added 24 h later. Cells were grown for 6 days with one growth medium change. At the end of the experiment, cells were lysed with the Cellytic Mammalian Cell Lysis/Extraction Reagent (Sigma, St. Louis, Mo.) and melanin was solubilized in 2N NaOH. Melanin content was determined spectrophotometrically at 405 nm and standardized to total protein content from the same cultures, using Bradford reagent (Sigma, St. Louis, Mo.). Kojic acid was used as positive control. Cell cultures were monitored on a Nikon Eclipse inverted microscope.

Tyrosinase activity was measured by the modified Pomerantz method (*Biophys Res Commun*, 1964). Mushroom Tyrosinase (Sigma #3212816630) stock enzyme was 5 U/well (25 U/ml). The substrate (1-DOPA, Fisher Scientific, Pittsburgh, Pa.) stock solution was 20 mM. Working solution was prepared in PBS for each assay. The reaction mixture consisted of 50 µl 20 mM I-DOPA and 10 µl undiluted test sample. Reaction was initiated by adding tyrosinase. Assays were preformed in 96 well flat-bottom microtiter plates (Fisher #0720087) and read at 490 nm after 5, 10, and 20 min.

Results: The test results of the melanin production and tyrosinase inhibition assays are summarized in Table 17 below. These results confirm that the tested materials can inhibit melanin production and tyrosinase activity.

TABLE 17

(Melanin Production Assay)

| Test Material | Melanin Inhibition in Cells | Dilution Factor | Tyrosinase inhibition assay (5 min) | Tyrosinase inhibition assay (10 min) | Tyrosinase inhibition assay (20 min) |
|---|---|---|---|---|---|
| $H_2O$ | 100% | — | 100.0 | 100.0 | 100.0 |
| Kojic acid | 83% | 200 µM | 39.0 | 35.5 | 33.1 |
| CLERILYS ™ | 60% | 1-100 | 62.4 | 45.9 | 34.3 |
| Ascorbyl Glucoside | 75-65.5% | 1/25-1/125 | 33.8 | 30.6 | 30.1 |
| UNINONTAN U34 ™ | 60.5% | 1/100 | 9.4 | 6.5 | 5.0 |

All of the compositions and/or methods disclosed and claimed in this specification can be made and executed without undue experimentation in light of the present disclosure. While the compositions and methods of this invention have been described in terms of specific embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 2,798,053
U.S. Pat. No. 3,755,560
U.S. Pat. No. 4,421,769
U.S. Pat. No. 4,509,949
U.S. Pat. No. 4,599,379
U.S. Pat. No. 4,628,078
U.S. Pat. No. 4,835,206
U.S. Pat. No. 4,849,484
U.S. Pat. No. 5,011,681
U.S. Pat. No. 5,084,563
U.S. Pat. No. 5,087,445
U.S. Pat. No. 5,100,660
U.S. Pat. No. 5,252,722
U.S. Pat. No. 5,272,136
U.S. Pat. No. 5,388,420
U.S. Pat. No. 5,432,161
U.S. Pat. No. 5,508,391
U.S. Pat. No. 5,559,146
U.S. Pat. No. 5,720,963
U.S. Pat. No. 5,843,907
U.S. Pat. No. 6,262,541
U.S. Pat. No. 6,290,938
U.S. Pat. No. 6,443,164
U.S. Pat. No. 6,447,760
U.S. Pat. No. 6,482,397
U.S. Pat. No. 6,495,126
Bai et al., *J. Biol. Chem.*, 278 (37):35501-35507, 2003.
Barany and Merrifield, In: *The Peptides*, Gross and Meienhofer (Eds.), Academic Press, NY, 1-284, 1979.
*Biophys. Res. Commun.*, 16 (2):188-94, 1964.
Figlar and Nooteboom, *Blumea*, 49:87-100, 2004.
Houghten et al., *Infect. Immun.*, 48 (3):735-740, 1985.
International Cosmetic Ingredient Dictionary, 10th Ed., 2004.
McCutcheon's Emulsifiers & Detergents North American Edition, 2001.
McCutcheon's Functional Materials North American Edition, 2001.
McCutcheon's, Detergents and Emulsifiers, North American Edition, 1986.
Merrifield, *Science*, 232 (4748):341-347, 1986.
Remington's Pharmaceutical Sciences, 18th Ed., Mack Printing Company, 1289-1329, 1990.
Schiltz et al., *J. Investigative Dermatology*, 87:663-667, 1986.
Stewart and Young, In: *Solid Phase Peptide Synthesis*, 2nd Ed., Pierce Chemical Co., 1984.
Tam et al., *J. Am. Chem. Soc.*, 105:6442, 1983.
Vollhardt and Schore, In: *Organic Chemistry*, 2nd Ed., W. H. Freeman & Co., 1994.

The invention claimed is:

1. A method of treating skin inflammation comprising topically applying to skin in need thereof a composition comprising:
   *magnolia officinalis* bark extract;
   *vitis vinifera* extract;
   tocopherol or tocopherol acetate; and
   hydrogenated lecithin, lecithin, or dextrin,
wherein the composition is not an anti-aging composition.

2. The method of claim 1, wherein the composition is in powdered form.

3. The method of claim 1, wherein the *vitis vinifera* extract is *vitis vinifera* seed extract.

4. The method of claim 3, wherein the composition does not include a magnolia flower extract.

* * * * *